United States Patent [19]

Deby et al.

[11] Patent Number: 5,846,799
[45] Date of Patent: Dec. 8, 1998

[54] HUMAN MYELOPEROXIDASE AND ITS THERAPEUTIC APPLICATION

[75] Inventors: Carol Deby, Liege; Joël Pincemail, Hony-Esneux; Alex Bollen, Itterbeek, all of Belgium

[73] Assignee: La Region Wallone, Brussels, Belgium

[21] Appl. No.: 109,471

[22] Filed: Aug. 20, 1993

Related U.S. Application Data

[63] Continuation of Ser. No. 460,931, Feb. 14, 1990, abandoned.

[30] Foreign Application Priority Data

Jun. 14, 1988 [FR] France ................................ 8807914

[51] Int. Cl.$^6$ ................... C12N 9/08; C12N 15/53; C12N 15/85
[52] U.S. Cl. ............... 435/192; 435/320.1; 536/23.2
[58] Field of Search ................. 435/192, 172.3, 435/69.1, 320.1; 536/23.2

[56] References Cited

U.S. PATENT DOCUMENTS 5,049,493 9/1991 Khosla et al. ................ 435/69.1

OTHER PUBLICATIONS

Morishita et al, *The Journal of Biological Chemistry*, vol. 262, pp. 3844–3851 (1987).
Matsuura et al, *J. Gen. Virol*, vol. 68, pp. 1233–1250 (1987).
Connors et al, *DNA*, vol. 7, pp. 651–661, (1988).
Structural and biological properties of human recombinant myeloperoxidase produced by Chinese hamster ovary cell lines, Moguilevsky et al., Eur. J. Biochem. 197:605–614.
Multiple Species of Myeloperidase Messenger RNAs Produced by Alternative Splicing and Differential Polyadenylation, Hashinaka et al., Biochemistry 1988, 27, 5906–5914.
Spectral and Enzymatic Properties of human REcombinant Myeloperoxidase: Comparison with teh Mature Enzyme, Jacquet et al., Archives of Biochmeistry and Biophysics, vol. 291, No. 1, Nov. 15, 1991, pp. 132–138.

Myeloperoxidase is synthesized as larger phosphorylated precursor, The EMBO Jornal, vol. 3, No. 11, 1984, pp. 2671–2676.

Characterization of cDNA clones for human myeloperoxidase:predicted amino acid sequence and evidence for multiple mRNA species, Johnson et al., Nucleic Acids Research, vol. 15, No. 5, 1987.

Identification and Properties of an Oxoferryl Structure in Myeloperoxidase Compound II, Oertling et al., Biochemistry 1988, vol. 27, pp. 5395–5400.

Candidicidal Activity of the Human Recombinant Myeloperoxidase System, Tournay et al., Antimicrobial Agents and Chemotherapy, Jan. 1993, vol. 37, No. 1.

Lethal oxidative damage to human immunodeficiency virus by human recombinant myeloperoxidase, Moguilevsky et al., FEBS Letters, vol. 302, No. 3, pp. 209–212.

Expression of a Synthetic Gene for Horseradish Peroxidase C in *Escherichia coli* and Folding and Activation of the REcombinant Enzyme with Ca$^2$ and Heme, Smith et al., The Journal of Biochemiustry, vol. 265, No. 22, Aug. 5, 1990, pp. 13335–13343.

(List continued on next page.)

*Primary Examiner*—Mindy Fleisher
*Assistant Examiner*—Philip W. Carter
*Attorney, Agent, or Firm*—Pollock, Vande Sande & Priddy

[57] ABSTRACT

A method of preparing biologically active human myeloperoxidase including the steps of preparing a vector for the expression of human myeloperoxidase. The vector includes plasmid pNIV2703. The plasmid includes a HindIII-SnaBI, HindIII-EcoRV or HindIII-HpaI cassette, the cassette including a complete DNA sequence for hMPO as shown in FIG. 1. CHO cells are transformed with the vector. The cells are cultured. The biologically active human myeloperoxidase is recovered.

6 Claims, 6 Drawing Sheets

OTHER PUBLICATIONS

Induction of nuetralizing antibodies by varicella–zoster virus gpII glycoprotein expressed from recombinant vaccinia virus, Massaer et al., Journal of General Virology 1993, vol. 74, pp. 491–494.

Expression of the human apolipoprotein AI gene fused to the *E. coli* gene for β–galactosidase, Lorenzetti et al., FEBS, vol. 194, No. 2 Jan. 1986.

Expression of Cloned Human Haptoglobin and $\alpha_1$–Antitrypsin Complementary DNAs in Saccharomyces cerevisiae, Van Der Straten et al., DNA, vol. 5, No. 2, 1986, pp. 129–136.

High–level Production of Fully Active Human α1–Antitrypsin in *Escherichia coli*, Johansen et al., Mol. Bio. Med. 1987, vol. 4, pp. 291–305.

Selection of Mutations that Increase α1–Antitrypsin Gene Expression in *Excherichia coli*, Sutiphong et al., Mol. Biol. Med. 1987, vol. 4, pp. 307–322.

Host System Pointers, Van Berunt, Biotechnology vol. 5, Jul. 1987, p. 664.

Synthesis and Localization of Myeloperoxidase Protein in Transfected BHK Cells, Cully et al., Experimental Cell Research 180, 1989 pp. 440–450.

Effect of nucleotide s=equences directly downstream from teh AUG on teh expression of bovine somatrotropine in *E. coli*, Tomich et al., Nucleic Acids REs. Apr. 25, 1989, vol. 17, No. 8, pp. 3179–3197 (Abstract Only).

Effect of von Willebrand factor coexpression on teh systhesis and secretion of factor VIII in Chinese hamster ovary cells, Kaufman et al., mol. Cell. Biol. Mar. 1989, vol. 9, No. 3, pp. 1233–1242 (Abstract Only).

Figure 1

```
Hind III                                     Nsi I
------   Met                                 ------
 AGCTTACCATGGGGGTTCCCTTCTTCTCTTCTCTCAGATGCATGGTGGACTTAGGACCTTGCTGGGCTGGGGGTCTCAC

TGCAGAGATGAAGCTGCTTCTGGCCCTAGCAGGCGTCCTGGCCATTCTGGCCACGCCCCAGCCCTCTGAAGGTGCTGCTC

CAGCTGTCCTGGGGGAGGTGGACACCTCGTTGGTGCTGAGCTCCATGGAGGAGGCCAAGCAGCTGGTGGACAAGGCCTAC

AAGGAGCGGCGGGAAAGCATCAAGCAGCGGCTTCGCAGCGGCTCAGCCAGCCCCATGGAACTCCTATCCTACTTCAAGCA

GCCGGTGGCAGCCACCAGGACGGCGGTGAGGGCCGCTGACTACCTGCACGTGGCTCTAGACCTGCTGGAGAGGAAGCTGC
                                                    Xba I
GGTCCCTGTGGCGAAGGCCATTCAATGTCACTGATGTGCTGACGCCCGCCCAGCTGAATGTGTTGTCCAAGTCAAGCGGC

TGCGCCTACCAGGACGTGGGGGTGACTTGCCCGGAGCAGGACAAATACCGCACCATCACCGGGATGTGCAACAACAGACG

CAGCCCCACGCTGGGGGCCTCCAACCGTGCCTTTGTGCGCTGGCTGCCGGCGGAGTATGAGGACGGCTTCTCTCTTCCCT

ACGGCTGGACGCCCGGGGTCAAGCGCAACGGCTTCCCGGTGGCTCTGGCTCGCGCGGTCTCCAACGAGATCGTGCGCTTC

CCCACTGATCAGCTGACTCCGGACCAGGAGCGCTCACTCATGTTCATGCAATGGGGCCAGCTGTTGGACCACGACCTCGA

CTTCACCCCTGAGCCGGCCGCCCGGGCCTCCTTCGTCACTGGCGTCAACTGCGAGACCAGCTGCGTTCAGCAGCCGCCCT

GCTTCCCGCTCAAGATCCCGCCCAATGACCCCCGCATCAAGAACCAAGCCGACTGCATCCCGTTCTTCCGCTCCTGCCCG

GCTTGCCCCGGGAGCAACATCACCATCCGCAACCAGATCAACGCGCTCACTTCCTTCGTGGACGCCAGCATGGTGTACGG

CAGCGAGGAGCCCCTGGCCAGGAACCTGCGCAACATGTCCAACCAGCTGGGGCTGCTGGCCGTCAACCAGCGCTTCCAAG

ACAACGGCCGGGCCCTGCTGCCCTTTGACAACCTGCACGATGACCCCTGTCTCCTCACCAACCGCTCAGCGCGCATCCCC

TGCTTCCTGGCAGGGGACACCCGTTCCAGTGAGATGCCCGAGCTCACCTCCATGCACACCCTCTTACTTCGGGAGCACAA

CCGGCTGGCCACAGAGCTCAAGAGCCTGAACCCTAGGTGGGATGGGGAGAGGCTCTACCAGGAAGCCCGGAAGATCGTGG

GGGCCATGGTCCAGATCATCACTTACCGGGACTACCTGCCCCTGGTGCTGGGGCCAACGGCCATGAGGAAGTACCTGCCC

ACGTACCGTTCCTACAATGACTCAGTGGACCCACGCATCGCCAACGTCTTCACCAATGCCTTCCGCTACGGCCACACCCT

CATCCAACCCTTCATGTTCCGCCTGGACAATCGGTACCAGCCCATGGAACCCAACCCCCGTGTCCCCCTCAGCAGGGTCT

TTTTTGCCTCCTGGAGGGTCGTGCTGGAAGGTGGCATTGACCCCATCCTCCGGGGCCTCATGGCCACCCCTGCCAAGCTG

AATCGTCAGAACCAAATTGCAGTGGATGAGATCCGGGAGCGATTGTTTGAGCAGGTCATGAGGATTGGGCTGGACCTGCC

TGCTCTGAACATGCAGCGCAGCAGGGACCACGGCCTCCCAGGATACAATGCCTGGAGGCGCTTCTGTGGGCTCCCGCAGC

CTGAAACTGTGGGCCAGCTGGGCACGGTGCTGAGGAACCTGAAATTGGCGAGGAAACTGATGGAGCAGTATGGCACGCCC

AACAACATCGACATCTGGATGGGCGGCGTGTCCGAGCCTCTGAAGCGCAAAGGCCGCGTGGGCCCACTCCTCGCCTGCAT

CATCGGTACCCAGTTCAGGAAGCTCCGGGATGGTGATCGGTTTTGGTGGGAGAACGAGGGTGTGTTCAGCATGCAGCAGC

GACAGGCCCTGGCCCAGATCTCATTGCCCCGGATCATCTGCGACAACACAGGCATCACCACCGTGTCTAAGAACAACATC
              Bgl II
TTCATGTCCAACTCATATCCCCGGGACTTTGTCAACTGCAGTACACTTCCTGCATTGAACCTGGCTTCCTGGAGGGAAGC

CTCCTGATATCTACGTATGGTT              Pst I
    ***          ------        ------
    ------SnaB I  Hpa I
    EcoR V
```

Figure 5
Vector pAcYM1

Figure 6

HUMAN MYELOPEROXIDASE AND ITS THERAPEUTIC APPLICATION

This application is a continuation of Ser. No. 07/460,931 filed on Feb. 14, 1990, now abandoned.

FIELD OF THE INVENTION

The present invention relates to the enzyme human myeloperoxidase (hMPO), to its preparation by genetic engineering and to its use by way of a medicinal product. It hence also relates to its use for the manufacture of pharmaceutical compositions containing it, as well as to the pharmaceutical compositions themselves.

More specifically, the therapeutic application in question relates to the treatment of immunodeficient patients in human therapy, by the reinforcement of antimicrobial activity at macrophage level, this applying in all cases of immune deficiencies whether caused, in particular, by AIDS, burns or irradiation.

BACKGROUND OF THE INVENTION

Resistance to infection by microorganisms makes use of non-specific functions (enzyme action, pH, epi-thelial wall) and of the adaptive immune responses of B and T lymphocytic cells.

The non-specific functions prevent invasion by the majority of attacking agents. However, when this first line of defense capitulates, the phagocytic system comes into operation, destroys the infectious agents and stimulates the immunity functions conferred by the B and T cells.

Any abnormality, hereditary or acquired, of the phagocytic system has serious consequences, since even microorganisms which are normally of low pathogenicity evade it and trigger recurrent infections.

Moreover, any deficiency in the immune system itself, at T or B cell level, leads to an enhanced susceptibility to intra- or extracellular viral and bacterial infections. These deficiencies may be hereditary or acquired (e.g. AIDS=elective T cell deficiency). Most people suffering from these deficiencies are subject to infection by opportunistic organisms (bacteria, protozoa, and the like).

In all cases of immunosuppression, it is hence desirable that the phagocytic system is as effective as possible, in order to limit the consequences of external attack. Of secondary importance under normal conditions, phagocytosis takes on an essential character when the B and T immune response weakens.

Among cells associated with the immune response, the polymorphonuclear leukocytes are of special interest in the context of combating infections. These cells contain an enzyme, myeloperoxidase, whose microbicidal action is well documented. Polymorphonuclear cells do not display any specificity with respect to an antigen, but play an essential part in the case of acute inflammation, with antibodies and the complement system, in the host's defense against microorganisms. Their main function is phagocytosis. During this process, the microorganisms are included in vacuoles (phagosomes) which fuse with the granules containing myeloperoxidase to form phagolysosomes. During phagocytosis, the enzymatic activity of the myeloperoxidase leads to the formation of HOCl, a potent bactericidal compound (hypochlorous acid); this activity requires $H_2O_2$ (hydrogen peroxide), which appears in the polymorphonuclear cell when it is stimulated by various agents, and in particular by the immunological reactions induced by microorganisms. Hypochlorous acid is oxidizing in itself, but produces still more strongly oxidizing derivatives, chloramines. Finally, reacting with $H_2O_2$, from which it is derived, hypochlorous acid produces an extremely oxidizing form of oxygen, singlet oxygen.

The major problem nevertheless lies at macrophage level. In effect, the macrophage is a very large cell, more robust than the polymorphonuclear cell and capable, like the latter, of phagocytosing microorganisms. It also possesses an $H_2O_2$-generating system but is not, however, capable of producing myeloperoxidase. This deficiency decreases its defensive efficacy. It has been discovered, however, according to the invention, that macrophages can incorporate and utilize myeloperoxidase, which remains active after penetration into the macrophages, an acquisition complementing in an effective manner their cytolytic and bacteriolytic arsenal, especially for the destruction of various infectious agents affecting immunosuppressed patients.

Although myeloperoxidase, once in the plasma, is taken up very quickly by the macrophages, specific administration systems delivering the enzyme in an optimal manner to the macrophages can be used according to the invention, producing myeloperoxidase conjugates by covalent coupling with a transporting agent possessing an affinity for macrophages. In this connection, there may be mentioned transporting agents such as mannosylated human albumin, as well as antibodies or antibody fragments, such as the Fc constant portion, directed towards receptors present on macrophages.

Other systems consist in coupling an antibody or Ab fragment specific for the macrophage to the enzyme human myeloperoxidase by non-covalent complexing or by DNA manipulation, to obtain an "immune complex".

The administration of such conjugates or immune complexes leads to targeting of the human MPO towards the macrophage, to its ingestion by phagocytosis and to release of the enzyme in active form within the macrophage, its preferential site of action, where it participates in combating infections.

In the case of immune complexes prepared by genetic engineering, DNA coding for MPO, the latter being active or in the form of a natural precursor, is coupled to DNA coding for an immunoglobulin fragment specifically recognizing macrophages.

SUMMARY OF THE INVENTION

The subject of the present invention is hence, by way of a medicinal product, a compound consisting of the enzyme human myeloperoxidase.

The subject of the invention is also, by way of a medicinal product, a compound consisting of a myeloperoxidase conjugate, by covalent coupling or complexing with a transporting agent possessing an affinity for macrophages, such as mannosylated human albumin or an antibody or antibody fragments, for example, the Fc constant portion directed towards receptors present on macrophages.

Another compound which is the subject of the present invention, delivering myeloperoxidase in an optimal manner to macrophages, also consists of liposomes, in particular biopolymerized liposomes, in which myeloperoxidase is encapsulated.

The medicinal products according to the invention are useful, in particular, for combating infections within macrophages.

Preferably, the enzyme human myeloperoxidase, used according to the invention, is of recombinant origin, that is to say prepared by genetic engineering.

Furthermore, the subject of the present invention is the use of the compounds according to the invention for the manufacture of pharmaceutical compositions useful, in particular, for the treatment of immunodeficiencies caused, in particular, by AIDS, burns or irradiation.

Finally, the subject of the present invention is pharmaceutical compositions comprising, by way of active principle, the compounds according to the invention.

The pharmaceutical compositions according to the invention may be presented in different forms, suitable for various forms of administration, in particular parenterally, systemically or topically, or by intravenous injection inasmuch as the target macrophages are present not only in the blood but also in other regions of the body.

The pharmaceutical compositions according to the invention then contain, apart from the active principle, pharmaceutically acceptable vehicles for the administration form in question.

Parenteral administration of myeloperoxidase or of compounds according to the invention is very suitable for the various immunosuppressive syndromes.

The decrease or elimination of natural immune barriers favors the appearance of infections due to pathogenic or opportunistic microorganisms.

Deficiencies in the immune system (for example T cell deficiencies, AIDS, irradiation, anticancer chemotherapy, etc.) are often associated with generalized infections (bacteria, mycoses, viral infections, protozoa, etc.) which are very difficult to control with only the existing antibiotic and chemotherapeutic agents. Under these conditions, myeloperoxidase can also be employed systemically in order to reinforce the antiseptic activity of the macrophages during phagocytosis. In effect, the experimental results indicate that macrophages and monocytes have an increased cytolytic and bacteriolytic activity in the presence of the enzyme.

Myeloperoxidase, or a compound according to the invention, may also be administered by topical application on, in particular, torpid ulcers, where the microvascularization is deficient (varicose ulcer).

For this topical application, the myeloperoxidase will be incorporated, for example, in water-based paste according to a known dermatological formulation. At the time of use, mixing of the myeloperoxidase suspension may be carried out, as required, with either dilute hydrogen peroxide solution (concentration 0.3%, for example)

or another enzyme such as xanthine oxidase. In this case, a $10^{-3}$M concentration of hypoxanthine, and optionally of ammonium chloride, should be added to the myeloperoxidase suspension. This mixture of pastes produces an evolution of HClO and a formation of amine chloride, which is especially effective for the cleansing or torpid wounds.

Other therapeutic indications may be envisaged for topical treatment:

1. The use of myeloperoxidase is advantageous in the prevention and treatment of intercurrent infections during burns caused thermally, chemically or by irradiation.
2. The phagocytic function appears to be deficient during atopic eczema. In this case, local application of the enzyme can have a beneficial stimulant action on the skin monocytes and macrophages.
3. Myeloperoxidase can have an adjuvant role in the treatment of gum infections, both in immunosuppressed subjects and during parodontoses.

According to the invention, the myeloperoxidase may be obtained by analytical purification from polymorphonuclear leukocytes. Nevertheless, advantageously, the enzyme human myeloperoxidase used will be produced by genetic engineering with recombinant DNA technology.

To this end, the essential stages are:

1) Construction of a library of cDNA clones which is representative of the products synthesized in leukocytic cells and screening of this library with a suitable probe characteristic of human myeloperoxidase. At the end of this operation, a cDNA clone coding for the enzyme is obtained.

2) The myeloperoxidase cDNA then has to be manipulated in order to permit its expression in various host/vector systems. A modular construction is mandatory if it is desired to be capable of assessing expression in systems as varied as *E. coli*, yeasts, mammalian cells or insect cells. The production of an active enzyme, correctly assembled and processed, is advantageously carried out in eukaryotic cell systems.

The subject of the present invention is hence also hMPO produced by culturing prokaryotic or eukaryotic cells transformed by a vector for the expression of hMPO in said cells.

Advantageously, the hMPO according to the invention is produced by cultures of higher eukaryotic cells, in particular by insect or mammalian cells.

Figure 5:
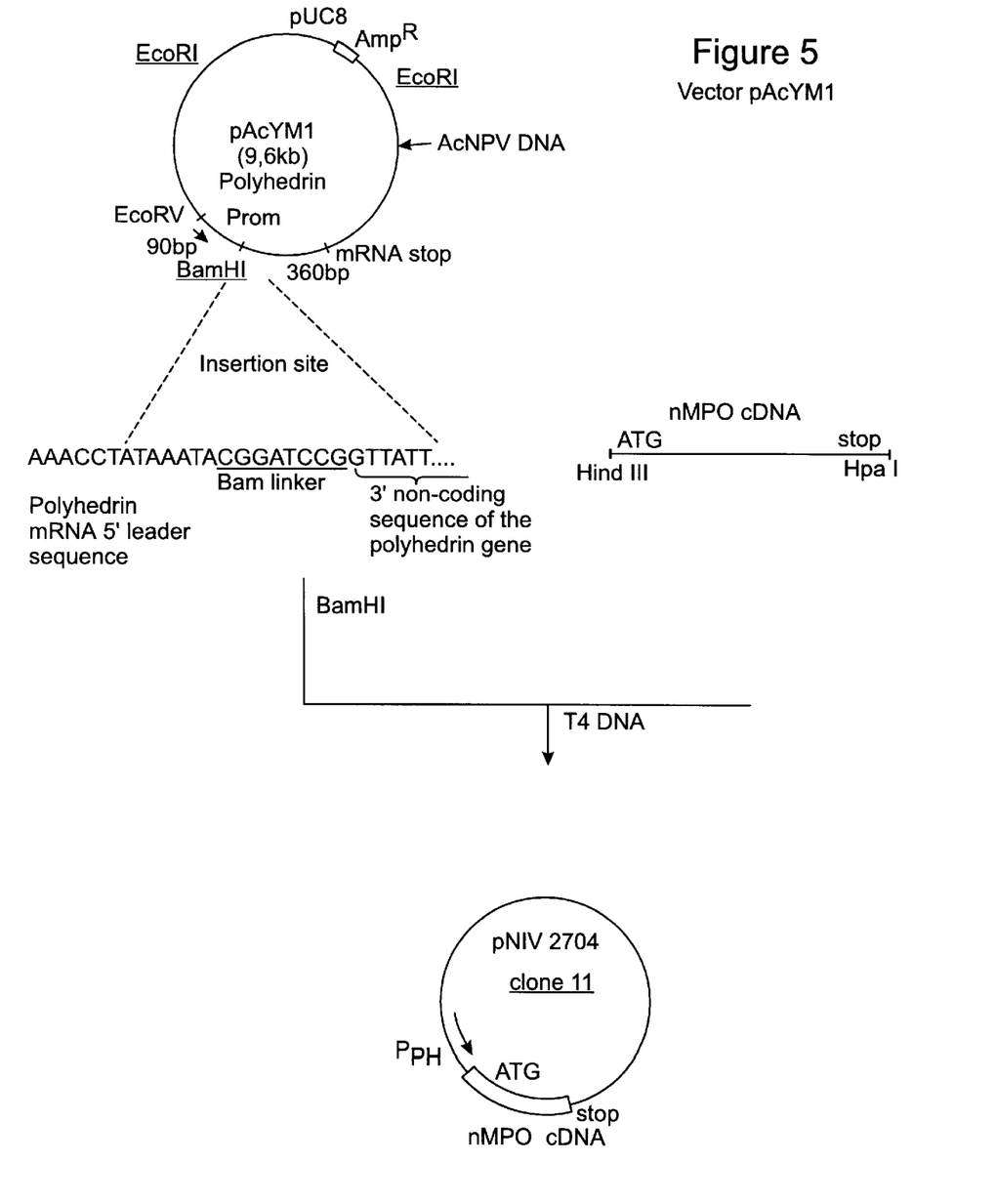
FIG. 5 shows the construction of the vector pAcYM1-MPO11 according to the invention (transfer plasmid for Baculovirus).

To this end, the subject of the present invention is:

1) a 2261-bp HindIII-SnaBI, HindIII-Eco.RV or HindIII-HpaI expression cassette carrying the coding sequence for hMPO as shown in FIG. 1, as well as plasmid pNIV2702 containing said cassettes, 2) a vector for expression in prokaryotic or eukaryotic cells containing said cassette, and especially 3) a recombinant transfer plasmid for Baculovirus containing the hMPO cDNA under the control of the polyhedrin promoter, in particular 4) plasmid pNIV2704 of FIG. 5, 5) insect cells, in particular of spodoptera frugiperda, such as Sf9 cells cotransfected by a vector according to the invention with wild-type viral DNA, and in particular cotransfected by plasmid pNIV2704, 6) insect cells, in particular of spodoptera frugiperda, such as Sf9 infected by a recombinant Baculovirus obtained with a vector according to the invention, in particular from plasmid pNIV2704, 7) hMPO produced by culturing insect cells, in particular of spodoptera frugiperda, such as Sf9 modified by a vector for expression in said cells according to the invention, 8) a vector for expression in mammalian cells, in particular CHO cells, containing the HindIII-SnaBI cassette of FIG. 1, in particular 9) a plasmid pNIV2703, 10) mammalian cells, in particular CHO cells, transfected by a vector for expression in said cells according to the invention, in particular by plasmid pNIV2703, and 11) hMPO produced by culturing mammalian cells, in particular CHO, transfected by a vector for expression in said cells according to the invention.

The detailed description which follow is designed to illustrate other features and advantages of the present invention.

BRIEF DESCRIPTION OF THE DRAWINGS

FIG. 1 shows the 2261-bp HindIII-HpaI cassette containing the sequences coding for human myeloperoxidase, and HindIII-SnaBI cassette.

The coding sequence begins at the ATG specifying the N-terminal methionine (Met) and ends with the TGA stop codon ( * * * ).

The sequences in bold type represent the synthetic oligonucleotides added at the 5' end and at the 3' end of the hMPO cDNA.

The 3 cassettes direct, respectively, the expression of the DHFR and Neo$^R$ selection markers, as well as that of a foreign cDNA (in the case illustrated above, it is that for t-PA). The latter cassette may be replaced by a cassette coding for any suitable cDNA, turning to good account the single restriction sites flanking the t-PA cassette.

DETAILED DESCRIPTION OF THE PREFERRED EMBODIMENTS

Abbreviations
SV early: early promoter of SV40;
5: non-coding extensions at the 5' end;
3: non-coding extensions at the 3' end;
SV: polyadenylation region of SV40;
Rous LTR: (long) terminal repeat sequence derived from Roux [sic] sarcoma virus;
bGH: polyadenylation region of the bovine growth hormone gene;
Betablopro [sic]: main promoter of murine β-globulin.

EXAMPLE 1

Preparation of hMPO by Genetic Engineering
A. Construction of a cassette containing the totality of the sequences coding for human myeloperoxidase flanked by restriction sites absent from the cDNA for myeloperoxidase (MPO)
1. Object Production of a HindIII/HpaI cassette containing the sequences coding for human MPO and which can be inserted in different expression vectors.
2. Starting material bacterial plasmid pMPO62 containing a complete cDNA for human MPO (Johnson et al., 1987, Nucleic Acids Research 15, 2013–2026);

any cloning vector containing appropriate restriction sites. Our choice fell on plasmid pTNDPC2, a plasmid derived from pTND (Connors et al., 1988, DNA 7, 651–661). Plasmid pTNDPC2 is not essential for obtaining said cassette; it would have been entirely possible to use another cloning vector containing the necessary restriction sites, such as plasmid pJRD184 (Heusterspreute et al., Gene 39 (1985) 299–309).
3. Production of oligonucleotides by chemical synthesis To obtain a HindIII site directly upstream from the hMPO ATG, we chose to synthesize, by means of chemical methods well known in our field, a pair of oligonucleotides which, when rehybridized with one another, contain, in the 5'-3' direction of the coding strand, a HindIII restriction site, the bases ACC, the sequences coding for the first 11 amino acids and the 1st base of the triplet of the twelfth amino acid of hMPO, which straddles an NsI1 site. These oligonucleotides are designated MPOIII and MPOIV (diagram 1 below).

To obtain an Hpa1 site downstream from the hMPO stop codon, a second pair of oligonucleotides was synthesized. When rehybridized, the latter have, in the 5'-3' direction on the coding strand, the last two bases of the triplet for amino acid 731, the sequence coding for the last 14 amino acids of hMPO, a stop codon (TGA) different from the natural stop codon of hMPO and fifteen bases containing an EcoRV site, an SnaBI site and the complement of an Hpa1 site. These oligonucleotides are designated MPOI and MPOII (diagram 1 below).

4. Subclonings

Subclonings 1

A 2053-bp (base pairs) NsI1-BglII fragment was extracted from plasmid pMPO62. This fragment and the 42-bp synthetic HindIII-Nsi1 fragment obtained by rehybridization of the oligonucleotides MPOIII and MPOIV were ligated to a 6755-bp HindIII-BglII fragment of pTNDPC2. The resulting plasmid pscMPO1 was introduced into *Escherichia coli* strain MM294, according to a wellknown method, with the object of producing plasmid pscMPO1 in larger amounts. Plasmid pscMPO1 thus contains a 2095-bp fragment extending from a HindIII site to a BglII site located approximately at amino acid 696 of hMPO.

Subcloning 2

A 1825-bp Xba1-Pst1 fragment was extracted from plasmid pMPO62. This fragment and the 62-bp synthetic Pst1-Hpa1 fragment obtained by rehybridization of the oligonucleotides MPOI and MPOII were ligated to a 3283-bp Xba1-Hpa1 fragment of TNDPC2. The resulting plasmid pscMPO2 was introduced into *Escherichia coli* strain MM294 with the object of producing it in larger amounts.

Plasmid pscMPO2 hence contains a 1887-bp fragment extending from an Xba1 site beginning with the first base for amino acid 123 of hMPO to an Hpa1 site.

5. Construction of plasmid pNIV2702 from pscMPO1 and pscMPO2

In order, finally, to obtain the HindIII-HPa1 hMPO cassette, a 374-bp HindIII-Xba1 fragment containing the sequence coding for amino acids 1 to 122 of hMPO and a 1887-bp Xba1-Hpa1 fragment containing the sequence coding for amino acids 123 to 745 of hMPO were extracted, respectively, from plasmid pscMPO1 and pscMPO2. These two fragments were then religated to a 5165-bp HindIII-Hpa1 fragment of TNDPC2 to obtain plasmid pNIV2702.

Plasmid pNIV2702 hence contains a 2261-bp HindIII-Hpa1 cassette carrying the totally of the sequences coding for hMPO (FIG. 1). This cassette can be readily extracted and transferred into different expression vectors for hamster ovary cells (CHO) or for insect cells (*Spodoptera frugiperda*) via the baculovirus.

Diagram 1

Figure 2:
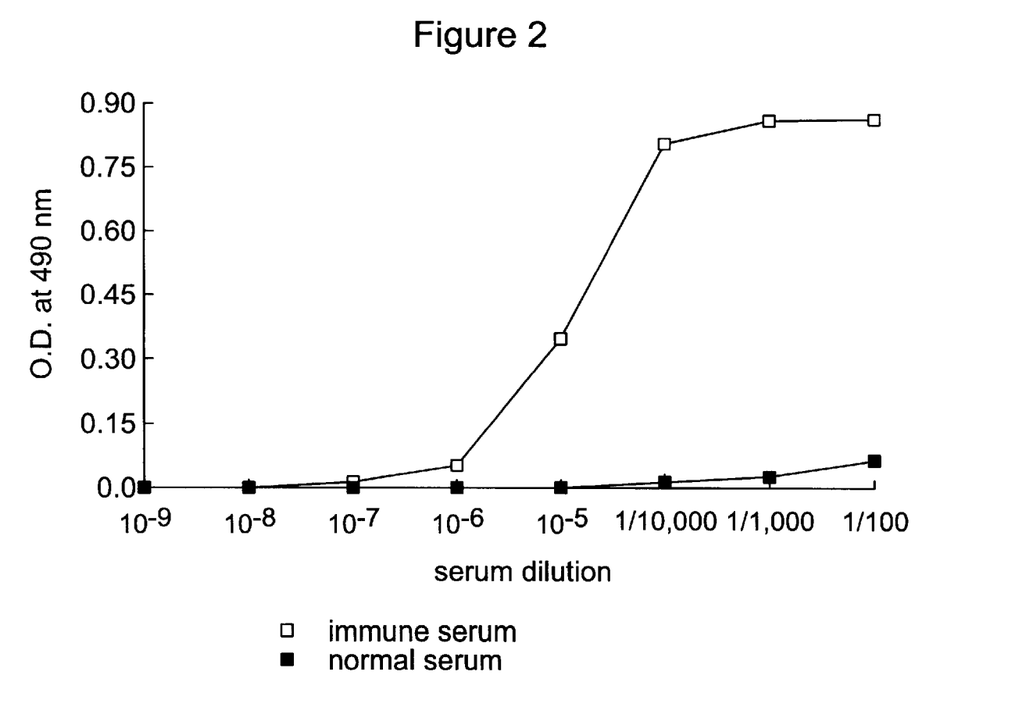
FIG. 2 shows the binding of rabbit sera in ELISA to MPO.
Figure 3:
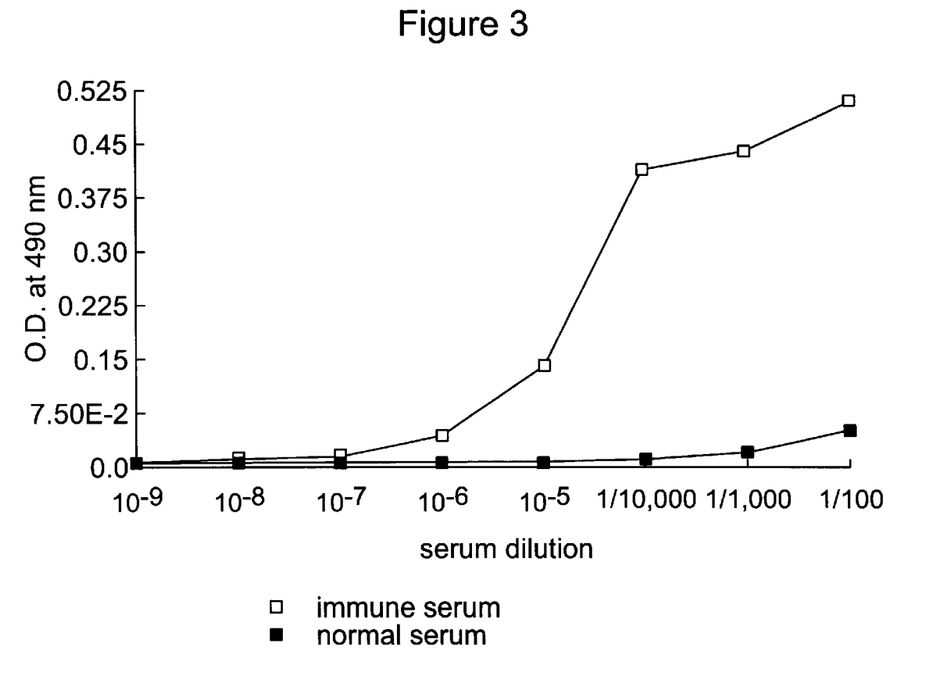
FIG. 3 shows the binding of mouse sera in ELISA to MPO.

B. Development of an ELISA test for the detection of natural and recombinant myeloperoxidase a) Production of anti-MPO antibodies Anti-MPO sera were obtained in rabbits and mice. They were tested in ELISA on MPO. (The plate is coated with MPO and saturated with BSA. The test antibodies are added, followed by an alkaline phosphatase/anti-Ig conjugate). In both cases, a titer of anti-MPO antibodies at least 8,000-fold higher in the immune serum than in a normal serum is obtained (FIGS. 2 and 3).

b) Development of the test

Figure 4:
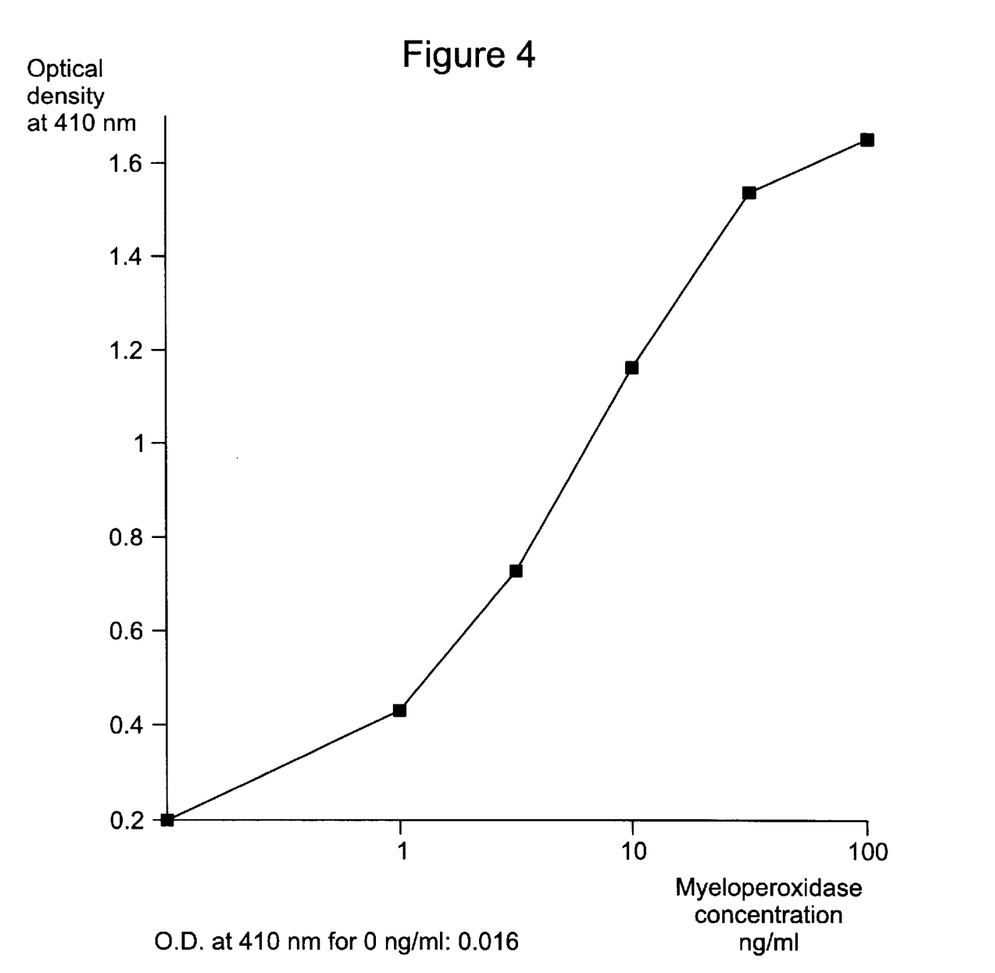
FIG. 4 shows a standard curve in an ELISA test for the detection of human myeloperoxidase.

A "sandwich" test was carried out using rabbit anti-MPO Ig (Prosan-Dakopatts A398) and one of our mouse anti-MPO sera. The plate is coated with rabbit Ig at a concentration of 7.6 gamma/ml in PBS pH 7.8, overnight at 4° C. It is saturated with 1% BSA in PBS pH 7.8/0.05% Tween 20 for 1 h 40 min at room temperature. The test samples are left for 2 hours at room temperature, followed by the mouse serum, diluted 1,000-fold in the saturation solution, for 2 h at room temperature, and finally alkaline phosphatase/rabbit antimouse Ig Fab2 conjugate (Prosan-Dakopatts D314) diluted 1,000-fold in TBS buffer (0.05M Tris-HCl pH 7.5, 0.15M NaCl) containing 1% BSA and 0.05% Tween 20. Between each step, the plate is washed 5 times with either TBS/0.05% Tween 20 (before and after application of the conjugate) or PBS/Tween 20 (other steps). Visualization is carried out by means of a solution of para-nitrophenyl phosphate at a concentration of 1 mg/ml in 10% diethanolamine, 0.01% $MgCl_2.6H_2O$, 0.02% $NaN_3$ pH9.8, and the reaction is stopped with 3M NaOH. Reading is carried out at 410 nm. FIG. 4 shows a binding curve for a pure MPO (Green Cross Corporation) diluted in an SFMJ insect cell culture supernatant (TC100 medium with 10% FCS). It is seen that the test is useful for assaying MPO in a concentration range of between 0.1 ng/ml and 100 ng/ml.

C) Cloning of MPO cDNA into the transfer plasmid for Baculovirus

The DNA of the transfer plasmid pAcYM1 (Baculovirus (ref.: Matsuura et al. J. Gen. Virol (1987) 68, 1233–1250 was linearized with BamHI and mixed with the 2261-bp HpaI-HindIII DNA fragment corresponding to MPO. The mixture was treated with T4 DNA polymerase, ligated and used for transforming competent E. coli MM294 cells. Selection of the cones was carried out by growth on ampicillin. After several contol [sic] enzyme restrictions on 48 clones, clone 11 was identified as having the MPO insert in the correct orientation relative to the polyhedrin promoter (pNIV2704) (FIG. 5).

The synthetic oligonucleotides/MPO junctions added at the 5' end and at the 3' end to the MPO cDNA during the above constructions were confirmed by sequencing these regions. The sequencing method on double-stranded DNA/a with sequenase was used.

Cotransfection and plaque assay

The recombinant plasmid 11 was used in conjunction with the wild-type viral DNA for cotransfecting Spodoptera frugiperda cells (Sf9) in culture (the protocol is well known and is detailed in the manual by M. D. Summers and G. E. Smith, "A Manual of Methods for Baculovirus Vectors and Insect Cell Culture Procedures, Texas University, College Station, 1987).

The cotransfection supernatants of days 5 and 7, after homologous recombination, were used in a plaque assay so as to have 100 to 1,000 lytic plaques per dish. The recombinant viruses not containing polyhedrin were identified 5 days later, visually or by DNA hybridization. 13 candiates were subcultured and purified.

Test of production of recombinant MPO

Two recombinant Baculoviruses, designated MPO1.1 and MPO05.2, were used for infecting Sf9 cells and measuring the capacity of the latter to produce myeloperoxidase. In both cases, the infected cells secrete into the culture medium a protein recognized specifically by antimyeloperoxidase antibodies, and the quantity of which was evaluated by an ELISA test at ≃0.2 µg/ml. (The infected cells were harvested at a density of $10^6$ cells/ml). The recombinant product was also to be found in the crude cell extract in the proportion of ≃0.06 µg/$10^6$ cells.

Cotransfection of Sf9 (Spodoptera frugiperda) insect cells.

Use of the recombinant vector (pNIV2704) pAcYM1/MPO 11 constructed, containing MPO downstream from the baculovirus promoter of polyhedrin, 100 µg used in conjunction with 1 µg of viral DNA.

Calcium chloride transfection technique

Use of the 5-d cotransfection supernatant for the plaque assay. Dilutions of −1 to −7, 5 dishes per dilution.

Use of the 7-d supernatant under the same conditions.

The harvested supernatants were used for producing lytic plaques in Sf9 cell monolayers (cell infection—-3 million per dish—with dilutions of the cotransfection supernatant, for 60'. Remove the inoculum and cast a layer of low melting point agar, 1.5% final. Cover with J. R. Scientific EX-Cell 400 medium with added antibiotics and leave in the incubator at 28° C. for 4 days). Staining of the dishes with neutral red after 4 d of infection and hybridization of filters with an

[$\alpha^{32}$P]-dCTP-labeled MPO DNA fragment. Subculturing of 13 candidates on the basis of autoradiography.

Two plaque assay purifications were then carried out successively.

D. Cloning of hMPO cDNA into the pTDN expression vector for mammalian cells (CHO) and introduction into the cells 1. Protocol
a—Production of the expression vector pNIV2703:

With the object of eliciting hMPO production by Chinese hamster ovary (CHO) cells, we introduced the 2253-bp HindIII-SnaBI cassette of pNIV2702 carrying the sequences coding for hMPO between the HindIII and SnaBI sites of the mammalian expression vector pTDN. The pTDN vector, the principle of use of which is identical to the pTND vector (Connors et al., 1988) from which it is derived, carries 2 genes encoding selection markers [resistance to neomycin (bacterial neophosphotransferase, Neo$^R$) and dihydrofolate reductase (DHFR)] and a cassette for expression of the molecule of interest, in this case ht-PA (human tissue plasminogen activator). The manipulation described above hence consists in replacing the HindIII-SnaBI cassette carrying the totality of the sequences coding for ht-PA by that encoding hMPO. When this replacement had been accomplished, the recombinant plasmid obtained, pNIV2703, accession number LMBP3510, deposited on Jul. 3, 1996, with the Belgian Coordinated Collections of Microorganisms (BCCM), Laboratorium voor Moleculaire Biologie—Plasmidencollectie (LMBP), Universiteit Gent, K. L.

Figure 6:
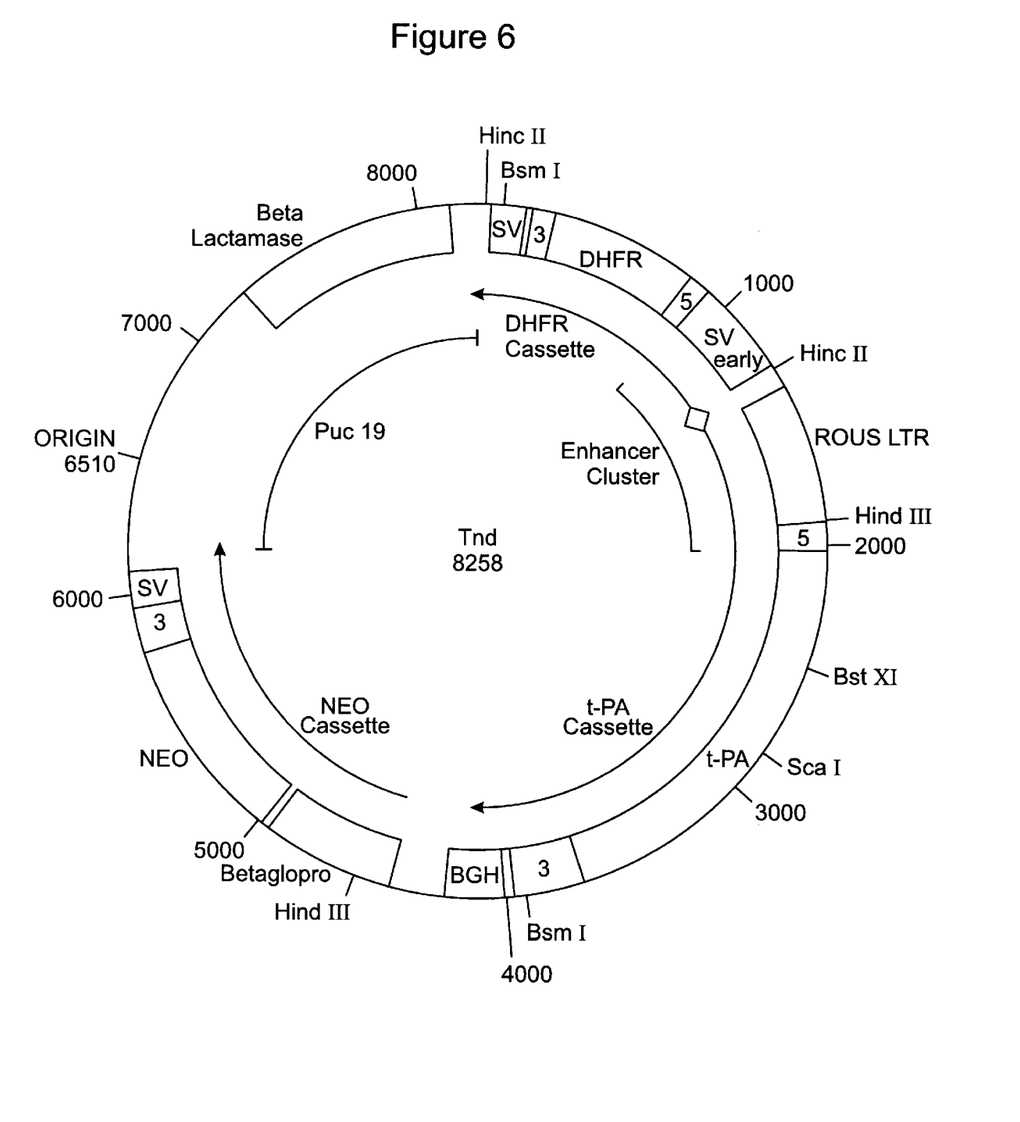
FIG. 6 shows the map of the Tnd vector from which plasmid pNIV2703 according to the invention is constructed.

Ledeganckstraat 35, B-9000 Gent, Belgium, was introduced into *E. coli* strain MM294 with the object of purifying it in a sufficient amount for the transfection of CHO cells. FIG. 6 depicts diagrammatically the pTND expression vector (Connors et al., 1988). The pTDN vector corresponds to the pTND vector apart from the fact that the DHFR cassette has a reverse reading order and is localized between the neo cassette and the t-PA cassette.

b—Transfection by electroporation of CHO cells:

By means of a digestion with the restriction enzyme Not 1, the sequences of bacterial origin (PUC19 in FIG. 6 were separated from the fragment carrying the 3 expression cassettes for mammalian cells. When digested, the vector pNIV2703 is introduced by electroporation, a method of transfection in CHO DHFR$^{31}$ cells according to a method similar to that described by Zerbib et al. (1985, Biochem. Biophys. Res. Comm. 129, 611–618). The cells were then placed in a growth medium containing G418, which does not permit the survival of cells not expressing the neophosphotransferase. Thus, after a period of 1 to 3 weeks, only the cells which have acquired the appropriate selection gene carried by the vector pNIV2703 survive and multiply. The cell clones thereby obtained were finally tested for the expression of hMPO. To this end, the culture supernatant and a cell extract of each of these clones was analyzed by means of an ELISA (Enzyme Linked Immunosorbent Assay) test enabling the hMPO to be qualified and quantified specifically.

The results show that the recombinant clones secrete recombinant MPO into the culture medium. The level of production, estimated by ELISA, is between 0.1 and 1 mg per ml of supernatant.

EXAMPLE 2
Therapeutic application of hMPO Role of leukocytic myeloperoxidase

Our body's defense against foreign microorganisms is effected by the white cells or leukocytes, including the lymphocytes which produce antibodies, the macrophages, eosinophils and neutrophils (or polymorphonuclear cells) which destroy the foreign microorganism by phagocytosis. During the latter, the neutrophils generate highly toxic and bactericidal oxygenated species: the superoxide anion, hydrogen peroxide, the hydroxyl radical and singlet oxygen.

The bactericidal action of hydrogen peroxide ($H_2O_2$) is increased one thousand-fold by myeloperoxidase (MPO), an enzyme localized in the azurophil (or primary) granules of neutrophils. In effect, this enzyme catalyzes, in the presence of $H_2O_2$, the oxidation of chloride ion ($Cl^-$) to generate hypochlorous acid (HOCl) (1) which has bactericidal properties.

Monocytes, which are macrophage precursors, possess a mechanism of antimicrobial activity similar to neutrophils, but they produce only small amounts of $H_2O_2$ and, furthermore, they possess approximately one third the amount of myeloperoxidase possessed by neutrophils (2). Moreover, in vitro experiments have shown that, during their maturation to macrophages, they completely lose their myeloperoxidase content, which also results in a decrease in the antibacterial activity (3). Thus, freshly isolated monocytes have a 90% cytotoxicity with respect to ingested *Toxoplasma gondii,* while macrophages (10 days of culture) display, at this stage of development, only 12% cytotoxicity.

However, several studies have shown that macrophages could phagocytose neutrophil cell debris (4, 5) and could thereby acquire myeloperoxidase activity, resulting in an increase in the toxicity of the small amount of hydrogen peroxide produced by the macrophages. Other studies have underlined the extent of the increase in the poroxidase [sic] activity of macrophages since, if *T. gondii* cells are incubated beforehand with horse eosinophil peroxidase, the macrophages then recover a 90% cytotoxicity, equivalent to that of monocytes (3, 6). The same observations have been made with *S. aureus* (7), *T. cruzi* (8) or tumor cells (9).

MATERIALS AND METHODS
Purification of human monocytes.

50 ml of blood of a normal subject are drawn onto Calciparine (0.3 ml containing 25,000 U/ml) and then diluted two-fold with 0.01M PBS buffer pH 7.2. 35 ml of diluted blood are then deposited on a density gradient consisting of 15 ml Ficoll-Paque (Pharmacia).

After centrifugation at room temperature at 1,800 rpm for 30 minutes, the lymphocytes and monocytes located at the gradient interface are recovered and stored on ice. The cells are then washed once with PBS buffer and thereafter centrifuged at 2,000 rpm for 10 minutes at 4° C. The operation is repeated twice more and the cells are then cultured.

Culturing of human monocytes.

The monocytes are purified by adhesion to glass. In cups 2.5 cm in diameter (Limbro), the cells are brought into contact with 1 ml of MEM culture medium containing 10% of human serum. After incubation at 37° C. for 2 hours in a 5% $CO_2$ atmosphere, the non-adherent cells (lymphocytes) are removed by drawing off the supernatant. The adherent monocytes are placed in contact again with 1 ml of MEM also containing 10% of human serum, and then left in culture.

I. Demonstration by microscopy of the incorporation of myeloperoxidase into monocytes I.1 Method The monocytes are brought into contact with 980 ng/ml of semi-purified human leukocytic myeloperoxidase. After 4 hours' incubation at 37° C., the MEM culture medium is removed and the monocytes are washed carefully with PBS buffer. The monocytes are then detached by vigorous agitation with 1 ml of PBS buffer and thereafter centrifuged so as to form a spot on a microscope slide.

The slides are fixed with ethanol/formaldehyde solution (9:1) at room temperature, then washed with water and thereafter air dried. The peroxidase activity of the monocytes is demonstrated by depositing a few drops of a mixture of 1% benzidine (30 ml), ten-fold diluted 4% sodium nitroprusside (0.3 ml) and 0.3 ml of 80-fold diluted $H_2O_2$ on the slide.

After 2 minutes' contact at room temperature, the slides are washed copiously with water and then air dried.

In a final step, the slides are stained with Giemsa to demonstrate the cells.

The slides are then examined under a microscope.

I.2 Results

Control monocytes display only very little positive reaction with benzidine.

Only a few monocytes develop a slightly brownish staining, thereby clearly demonstrating that myeloperoxidase is present in only small amounts in these cells.

In contrast, monocytes cultured for 24 hours and brought into contact with myeloperoxidase react positively and very distinctly with benzidine. These first results confirm an incorporation of myeloperoxidase by simple phagocytosis into monocytes.

II. Demonstration by radioimmunoassay of the incoporation of myeloperoxidase by monocytes II.1 Method After adherent monocytes have been brought into contact with 1 ml of MOM buffer containing semi-purified myeloperoxidase, or neutrophil debris obtained by sonication (the protocol of four experiments is described in detail in the results), the supernatant is recovered and then centrifuged at 2,000 rpm for 10 minutes in order to recover monocytes which may possibly have become detached (pellet 1).

The adherent monocytes are detached by efficient agitation with 1 ml of PBS buffer. They are added to pellet 1 and then centrifuged at 2,000 rpm for 10 minutes at 4° C. After three washes with PBS buffer, the cells are counted and then diluted so as to obtain 3 million monocytes per ml.

The myeloperoxidase of the monocytes is solubilized by treating the cells with cetyltrimethylammonium bromide (0.01%) and by two successive freezings.

After return to room temperature, 100 µl of the medium are withdrawn for quantification of the enzyme according to a specific radioimmunoassay technique (10).

II.2 Results

Experiment 1

Three million monocytes, cultured for 24 hours, are brought into contact for 2 hours with 1 ml of MEM culture medium containing: p1 a) MPO 1=semi-purified myeloperoxidase at a concentration of 980 ng/ml.

b) MPO 2=50 µl of a concentrated suspension of sonicated neutrophil debris.

| 1 | | myeloperoxidase ng/ml | % increase in the intracellular content |
|---|---|---|---|
| Monocytes 24 h (3 million) | | 80 | |
| Monocytes 24 h + MPO 1 | 2 hours' incubation | 88 | 1.1 |
| Monocytes 24 h + MPO 2 | | 358 | 447 |

The base-line level of monocytes which have not been brought into contact with myeloperoxidase is 80 ng/ml. After 2 hours' incubation with semi-purified myeloperoxidase, the intracellular myeloperoxidase level of the monocytes remains unchanged. In contrast, a strong increase (447% of the base-line level) in the intracellular myeloperoxidase concentration is observed when the monocytes are brought into contact with neutrophil debris. The latter observation shows that monocytes are indeed capable of phagocytosing neutrophil debris.

Experiment 2

The conditions are identical to those in Experiment 1, except that the incubation time is 4 hours. In this instance, a marked increase (440%) is noted in the intracellular myeloperoxidase content of monocytes which have been brought into contact with the enzyme. Similarly, the neutrophil debris is to phagocytose [sic] even better than in the previous experiment, since there is a 2,070% increase in the intracellular myeloperoxidase content.

| 2 | | myeloperoxidase ng/ml | % increase in the intracellular content |
|---|---|---|---|
| Monocytes 24 h (3 million) | | 54 | |
| Monocytes 24 h + MPO 1 | 4 hours' incubation | 238 | 440 |
| Monocytes 24 h + MPO 2 | | 1,120 | 2,070 |

Experiment 3

The table below shows that monocytes cultured for 48 hours incorporate myeloperoxidase or neutrophil debris better after 2 hours' incubation than monocytes cultured for 24 hours.

| 3 | | myeloperoxidase ng/ml | % increase in the intracellular content |
|---|---|---|---|
| Monocytes 48 h (3 million) | | 102 | |
| Monocytes 48 h + MPO 1 | 2 hours' incubation | 204 | 220 |
| Monocytes 48 h + MPO 2 | | 788 | 772 |

Experiment 4

Monocytes cultured for 24 hours are, in this instance, brought into contact for 2 hours and 6 hours with 1 ml of culture buffer containing 3,920 ng/ml of semi-purified myeloperoxidase (MPO3).

| 4 | myeloperoxidase | | % increase in the cell content |
|---|---|---|---|
| | ng/ml | U/ml | |
| Monocytes 24 h (3 million) | 90 | 0.6 | |
| Monocytes 24 h + MPO 3 (2 hours' incubation) | 136 | 0.86 | 151 |
| Monocytes 24 h + MPO 3 (6 hours' incubation) | 324 | 1.3 | 360 |

After being brought into contact with the enzyme for 2 hours, the monocytes increase their intracellular content by 151%, whereas, in Experiment 1, this content has remained unchanged. The increase is still more marked after being brought into contasct for 6 hours. In this experiment, the enzymatic activity of the myeloperoxidase, determined by the oxidation of o-dianisidino [sic] in the presence of $H_2O_2$, was also measured. The base-line level of 0.6 U/ml increases as the contact time increases (value doubled after 6 hours). This finding is proof that exogenous myeloperoxidase incorporated into monocytes indeed remains enzymatically active. III. Cytotoxicity of monocytes which incorporated myeloperoxidase with respect to schistosomula III.1 Method The schistosomula are isolated from cercariae by an artificial technique (filtration through a piece of mouse skin). The following experimental protocol was adopted: 24-hour monocytes are incubated for 2 hours with myeloperoxidase and then washed carefully with MEM culture medium. The monocytes, treated or otherwise with myeloperoxidase, are then incubated for 6 hours with serum of a subject suffering from bilharziosis (10%) or with a serum of a healthy subject (10%) which serves as a control (inherent effect of the serum). Schistosomula, treated beforehand or otherwise with myeloperoxidase, are then added to the culture medium. After 16 hours, the live and dead schistosomula are counted and a % cytotoxicity of the monocytes is thereby determined. Monocytes: 100 to 200,000 cells cultured for 24 hours Experiment 5

These results show that the cytotoxicity of monocytes which have previously incorporated MPO 1 or MPO 2 with respect to shistosomula in the presence of bilharziosis serum is increased by 50% compared to control monocytes. The true percentage cytotoxicity is obtained by subtracting the value obtained with healthy serum (inherent effect of the serum) from the value obtained with the bilharziosis serum.

| 5 | % cytotoxicity of monocytes | | |
|---|---|---|---|
|  | without MPO | + MPO 1 | + MPO 2 |
| bilharziosis serum, 10% | 42.5 ± 5 | 70.5 ± 10.5 | 71.5 ± 3 |
| healthy serum, 10% | 19 ± 0 | 26 ± 1.4 | 25 ± 5 |
| true % cytotoxicity | 23.5 | 44.5 | 46.5 |

Experiment 6

In this experiment, a comparison was made between the cytotoxicity of monocytes which had or had not incorporated myeloperoxidase with respect to normal schistosomula (stimulus 1) and schistosomula which had been brought into contact beforehand for 2 hours with 980 ng/ml of myeloperoxidase (stimulus 2).

| 6 | % cytotoxicity of monocytes | | | |
|---|---|---|---|---|
|  | without MPO | | + MPO 1 | |
|  | stimulus 1 | stimulus 2 | stimulus 1 | stimulus 2 |
| bilharziosis serum, 10% | 42.5 ± 5 | 62.5 ± 2 | 70.5 ± 10.5 | 99 |
| healthy serum, 10% | 19 ± 0 | 22 ± 4 | 26 ± 1.4 | 35.5 ± 2 |
| true % cytotoxicity | 23.5 | 40.5 | 44.5 | 64 |

Monocytes not treated with myeloperoxidase have a cytotoxicity which rises from 23.5 to 40.5% when they are brought into contact with schistosomula coated with myeloperoxidase.

Although the model is different (in this case, the monocyte does not kill the schistosomulum by phagocytosis but by simple adhesion to it), this observation is in agreement with previous work showing that the cytotoxicity of macrophages is increased when the infectious organism (*T. gondii*) phagocytosed is coated with a peroxidase (3, 6).

The combination of monocytes which have incorporated myeloperoxidase with schistosomula coated with the enzyme enables a very high cytotoxicity (64%) to be obtained.

Conclusions

It was only shown in the literature that monocytes can acquire an accompanied peroxidase, that is to say a peroxidase associated with a support which is a microorganism, and can thereby undergo an increase in their cytotoxicity with respect to a whole series of infectious organisms. In these experiments, it should, in effect, be noted that the myeloperoxidase was first linked to the infectious organism, which was then ingested by the monocyte or macrophage.

According to the invention, human granulocytic myeloperoxidase has been used, and it has been discovered that:

1) myeloperoxidase can be phagocytosed directly without the intervention of an activator by the monocyte, 2) the ingested enzyme remains enzymatically highly active, as shown by the results on cytotoxicity with respect to schistosomula.

These observations indicate that exogenous myeloperoxidase administered to the body will be taken up by human monocytes or macrophages, and can consequently be used as a therapeutic means in patients suffering from deficiencies, hereditary (agranulocytosis) or acquired (AIDS).

REFERENCES

1. Zgliczynski J. M., Stelmaseynska, T., Domanski J. and Cstrowski W. Chloramines as intermediates of oxidative reaction of amino acids by myeloperoxidase. Biochim Biophys Acta 1971, 235:419–424.
2. Bos A., Wever R., and Roos D., Characterization and quantification of the peroxidase in human monocytes. Biochim Biophys Acta 1978, 525:37–44.
3. Locksley R. M., Nelson C. S., Fankhauser J. E. and Klebanoff S. J. Loss of granule myeloperoxidase during in vitro culture of human monocytes correlates with decay in antiprotozoa activity. Am J Trop Hyg 1987. 36(3):541–548.
4. Hoifets L., Katsuyuki I. and Mayer G. Expression of peroxidase-dependent iodination by macrophages ingesting neutrophils debris. J. Reticuloendothel Soc 1980, 28(3):391–404.
5. Atwal O. Cytoenzymological behavior of peritoneal exudate cells of rat in vivo. J. Reticuloendothel Soc 1971, 10:163–172.
6. Locksley R. M., Wilson C. B. and Klebanoff S. J. Role of endogenous and acquired peroxidase in the toxoplasmacidal activity of murine and human mononuclear phagocytes. J. Clin Invost 1982, 69:1099–1111.
7. Ramsey P. G., Martin T., Chi E. and Klebanoff S. J. Arming of mononuclear phagocytes by eosinophil peroxidase bound to staphylococcus aureus. J. Immonol 1982, 128:415–420.
8. Nogueira N. H., Klebanoff S. J. and Cohn Z. A. Teruzi : sensitization to macrophage killing by eosinophil peroxidase. J Immunol 1982, 128:1705–1708.
9. Nathan C. F. and Klebanoff S. J. Augmentation of spontaneous macrophage-mediated cytolysis of eosionophil peroxidase, J Exp Med 1982, 155:1291–1308.
10. Deby-Dupont G., Pincemail J., Thirion A. and Deby C. A radioimmunoassay for polymorphonuclear leucocytes myeloperoxidase : preliminary results. Arch Int Physiol Biochem 1987 (in press).

We claim:

1. A method of preparing biologically active human myeloperoxidase, said method comprising the steps of:

preparing a vector for the expression of human myeloperoxidase, said vector comprising plasmid pNIV2703, said plasmid including a HindIII-SnaBI, HindIII-EcoRV or HindIII-HpaI cassette, said cassette including a complete DNA sequence for hMPO as shown in FIG. 1;

transforming CHO cells with said vector;

culturing said cells; and recovering said biologically active human myeloperoxidase.

2. The method according to claim 1, wherein said biologically active human myeloperoxidase is free and not conjugated to another molecule.

3. The method according to claim 1, further comprising the step of conjugating said biologically active human myeloperoxidase to another molecule.

4. The method according to claim 3, wherein said biologically active human myeloperoxidase is conjugated by covalent coupling or complexing to a transporting agent possessing an affinity for macrophages.

5. The method according to claim 4, wherein said transporting agent includes at least one member selected from the group consisting of mannosylated human albumin and an antibody fragment; and said transporting agent being directed towards receptors present on macrophages.

6. The method according to claim 1, further comprising the step of encapsulating said biologically active human myeloperoxidase in liposomes.

* * * * *